United States Patent [19]

Peterson

[11] Patent Number: 5,562,648
[45] Date of Patent: Oct. 8, 1996

[54] ADULT INCONTINENT ABSORBENT UNDERGARMENT

[75] Inventor: Robert H. Peterson, Hendersonville, Tenn.

[73] Assignee: E. I. Du Pont de Nemours and Company, Wilmington, Del.

[21] Appl. No.: 414,251

[22] Filed: Mar. 31, 1995

[51] Int. Cl.⁶ ........................................................ A61F 13/15
[52] U.S. Cl. ............................................. 604/370; 604/393
[58] Field of Search ................................. 604/370, 385.1, 604/393, 397

[56] References Cited

U.S. PATENT DOCUMENTS

| | | | |
|---|---|---|---|
| Re. 33,351 | 9/1990 | Papajohn | 604/397 |
| 4,578,070 | 3/1986 | Holtman | 604/385.1 |
| 5,141,794 | 8/1992 | Arroyo | 604/370 |
| 5,187,952 | 2/1993 | Zafiroglu | 66/192 |
| 5,246,433 | 9/1993 | Hasse et al. | 604/396 |
| 5,247,893 | 9/1993 | Zafiroglu | 112/262.1 |
| 5,350,625 | 9/1994 | Peterson et al. | 428/219 |
| 5,368,585 | 11/1994 | Dokken | 604/393 |
| 5,370,634 | 12/1994 | Ando et al. | 604/385.1 |
| 5,389,095 | 2/1995 | Suzuki et al. | 604/385.2 |

*Primary Examiner*—Robert A. H. Clarke

[57] ABSTRACT

An improved reusable adult incontinent absorbent undergarment involving an outer panty with elastic waist band and leg holes and an inner hour-glass shaped insert stitched or attached by the use of VELCRO fasteners to the back and front of the panty without stitching in the crotch. By employing a novel combination of multiple layers of highly absorbent, antimicrobial fabric with an open knit polyester making contact with the skin forming a pad that is free floating in the crotch and an outer non-woven layer of urethane coated stretch fabric as a waterproof liner that is separately free floating and elasticly gathered in the crotch, the propensity for fluid leakage during use is dramatically reduced.

4 Claims, 1 Drawing Sheet

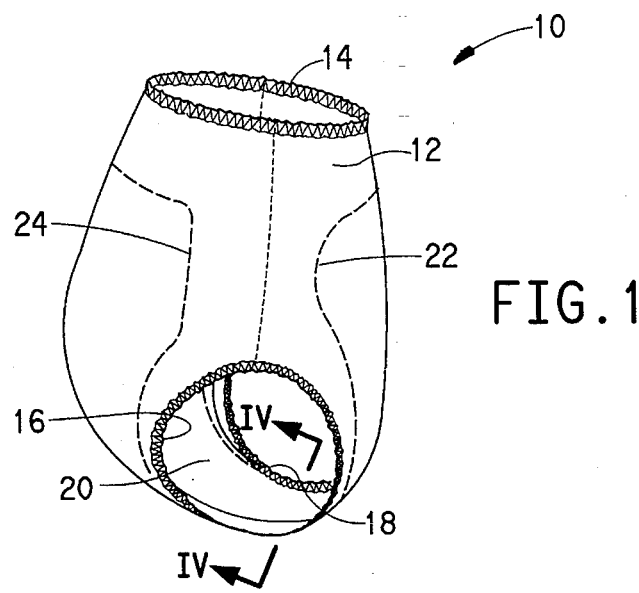
FIG. 1
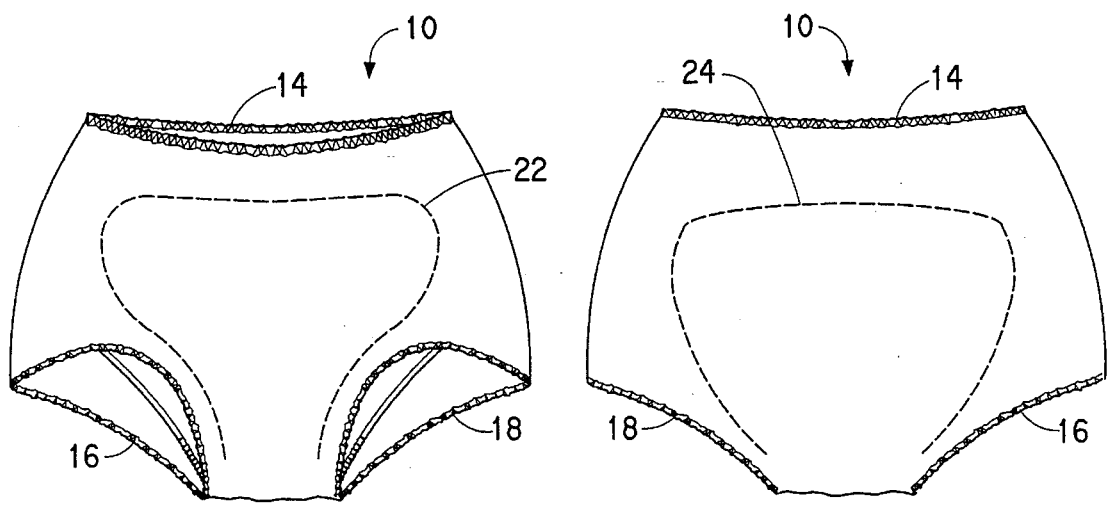
FIG. 2
FIG. 3
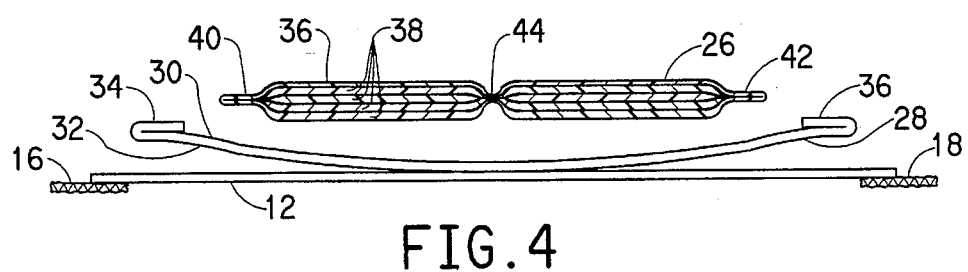
FIG. 4

ADULT INCONTINENT ABSORBENT UNDERGARMENT

BACKGROUND OF THE INVENTION

1. Field of the Invention

This invention relates to an improved adult incontinent absorbent undergarment. More specifically but not by way of limitation, the invention relates to a reusable absorbent panty involving multiple layers of fabric (e.g., eight layer construction) including a double protection floating crotch with laminated absorbent pad and separate waterproof inner liner.

2. Description of the Related Art

In general, many kinds of disposable diapers as well as reusable incontinent undergarments have been proposed in the past, Also, with the advent of modem textiles and fabrics various multi-layered reusable adult incontinent undergarments have been proposed and commercially sold with varying degrees of product acceptance and success. One particular problem with such garments has been the tendency for stitching to result in leakage during use. As such, there exists a need for an improved adult reusable incontinent undergarment that takes full advantage of modem fabrics and simultaneously avoids the problems associated with leakage at stitch seams and the like.

SUMMARY OF THE INVENTION

In view of the above, the present invention provides an improved adult incontinent undergarment comprising:

(a) an outer panty having elastic top around the waist and elastic edging around the leg holes wherein said outer panty fabric consists of a conformable, stretchable fabric that is absorbent and adapted to wick moisture; and (b) an inner hour-glass shaped insert operatively attached to the inside surface of said panty at the perimeter of the large ends of said hour-glass shaped insert to the back and front area of said panty, respectively, and not operatively attached to the inside surface of said outer panty at the narrow portion of the hour-glass shaped insert to the crotch of said panty, wherein said hour-glass shaped insert comprises:

(i) an inner most wicking layer of open knit fabric for making contact to the skin;

(ii) a plurality of center layers of spunlaced fabric comprising a blend of antimicrobial acrylic fibers and hydrophilic cellulosic fibers, wherein the edges of said plurality of layers and said open knit layer are stitched together in the region of the crotch forming a separate free-floating absorbent fabric pad at the crotch; and (iii) a outer most layer of non-woven, conformable fabric, wherein the outer surface of said non-woven fabric is laminated with a moisture impermeable coating of urethane and the edges of said non-woven fabric are stitched around individual elastic bands in the region of the crotch that tend to gather the urethane coated non-woven, conformable fabric forming a separate free-floating waterproof barrier between the panty and said absorbent fabric pad at the crotch.

In one embodiment of the adult incontinent undergarment according to the instant invention, the inner hour-glass shaped insert is operatively attached to the inside surface of the outer panty by stitching the perimeter of the large ends to the back and front area of the outer panty. In another embodiment, the inner hour-glass shaped insert is operatively attached by the use of "VELCRO" fasteners. In a particularly preferred embodiment the inner hour-glass shaped insert further comprises two to six (most preferrably four) center layers of a spunlaced water-absorbent fabric comprising a mixture acrylic and cellulosic fibers consisting essentially of about 25 to less than 50 percent, by weight, of crimped antimicrobial acrylic fibers having a dpf (denier per fiber) of about 0.75 to about 3.0 and a length from about 0.75 to about 3.0 inches and about 75 to greater than 50 percent of crimped hydrophilic cellulosic fibers having a dpf of about 0.75 to about 3.0 and a length from about 0.75 to about 3.0 inches. In a further preferred embodiment the inner most wicking layer of open knit fabric for making contact to the skin is polyester fabric made of four-channel fiber.

Thus, it is the primary object of the present invention to provide an improved reusable adult incontinent undergarment that employs a highly absorbent multi-layered fabric composite and a construction technique that virtually avoids all leakage at stitched seams and the like.

BRIEF DESCRIPTION OF THE DRAWING

FIG. 1 is a side view of an adult incontinent under garment according to the present invention.

FIG. 2 is a front view of the adult incontinent under garment shown in FIG. 1.

FIG. 3 is a rear view of the adult incontinent under garment shown in FIG. 1.

FIG. 4 is a cross-sectional view of the crotch of the adult incontinent under garment shown in FIG. 1 illustrating the multiple layers of fabric including the double protection floating crotch with laminated absorbent pad and separate waterproof inner liner, all as seen through line IV—IV.

DESCRIPTION OF THE PREFERRED EMBODIMENTS

The improved adult incontinent under garment according to the present invention, how it is made and functions and how the overall article differs from prior art as well as its advantages relative to the prior art can perhaps be best explained and understood by reference to the drawing. As illustrated in FIG. 1, the adult incontinent under garment (generally designated by the number 10) involves an outer panty 12 having an elastic top 14 around the waist and elastic edgings 16 and 18 around the leg holes. This outer panty is preferably manufactured using a stretchable, absorbent fabric that tends to conform to the body. Typically the fabric is characterized as being a comfort fabric in that it will absorb and wick moisture in the form of perspiration and the like while retaining a comfortable fit so that the garment will stay in place. The choice of fabric for the outer panty will include various natural or synthetic fibers and blends thereof as generally known in the art. Particularly suitable fabrics for the manufacture of the outer panty include, by way of example but not by way of limitation, a stitchbonded non-woven "XYMID" style 4078 fabric stitched with nylon covered "LYCRA" and marketed under the name "COMFORSPAN" by E.I. Du Pont de Nemours & Company. The elastic waist band 14 and the leg hole edgings 16 and 18 are to be manufactured using robber or robber containing material as generally known in the art and are to be sized to facilitated containment of liquids.

As further illustrated in the drawing, an inner hour-glass shaped insert 20 is attached to the inside surface of the outer panty 12 by stitching the perimeter of the large ends 22 and 24 of the hour-glass shape to the front (see FIG. 2) and the back (see FIG. 3) of the panty, respectively. Alternatively, the insert can be attached to the front and back of the outer panty by use of "VELCRO" fasteners or the like (not shown). The narrow portion of the hour-glass shaped insert located in the crotch area is intentionally free of stitching and needle holes. In this manner the insert 20 is free-floating in the crotch area.

As illustrated in the cross-sectional view of FIG. 4, the hourglass shaped insert 20 involves multiple layers of fabric and in the crotch area the presence of two separate free-floating layered composites 26 and 28. The outer most (i.e., furthest from the skin of the user) composite 28 consists of a light weight, non-woven fabric layer 30 wherein the outer surface of the non-woven fabric is laminated with a moisture impermeable coating of urethane 32. Also, as suggested in the drawing the edges of this non-woven fabric are, in the area of the crotch, stitched around individual elastic bands 34 and 36 that tend to gather the urethane coated non-woven, free-floating portion of composite layer 28. This in turn forms a waterproof barrier between the outer panty 12 and the inner absorbent layered pad composite 26. The free-floating layered composite 28 is intentionally sized in the area of the crotch such that it is slightly wider than inner composite pad 26 and slightly longer than pad 26 thus accounting for the presence of gathering of the urethane coated fabric. In this manner a fluid containment barrier free of needle holes is inherently created when in use. The remainder of the perimeter of the layered composites 26 and 28 are essentially identical and overlapping such that together they form a single insert 20 which is stitched (22 and 24) as a unit to the front and back of panty 12 (again and alternatively the insert could be fastened by "VELCRO" rather than being stitched). The choice of fabric for this outer light weight, non-woven stretchable fabric layer 30 will include various natural or synthetic fibers and blends thereof as generally known in the art. Particularly suitable fabrics for the manufacture of the outer layer include, by way of example but not by way of limitation, a "SONTARA" based stretch "XYMID" fabric marketed by E.I. Du Pont de Nemours & Company. The urethane coating 32 can be chosen from any such elastomeric material as generally known in the art.

As illustrated in the cross-sectional view of FIG. 4, the absorbent pad layered composite 26 consists of a top (inner most) layer 36 of open knit fabric and a plurality (four as shown in this specific embodiment) of highly absorbent center layers 38. The outer edge 40 and 42 of these respective layers are stitched to each other thus forming a unitary pad that is separately free-floating in the crotch area. Optionally, this pad is sewn together along the longitudinal line 44 from the top of the hour-glass to the bottom thus further enhancing the structural integrity of the absorbent pad portion of the insert 20 without needle holes in the urethane coated moisture barrier layer 28. The choice of fabric for the inner most open knit fabric layer will include various natural or synthetic fibers and blends thereof as generally known in the art. Particularly suitable fabric for the manufacture of the inner layer includes, by way of example but not by way of limitation, a very light, open knit structure of polyester fabric made from four-channel fibers marketed by E.I. Du Pont de Nemours & Company under the certification mark "COOLMAX". Alternatively, a highly absorbent polypropylene fabric or similar fabric made of cellulose acetate fiber can be used as the inner layer and should be considered equivalent for purposes of this invention. The choice of fabric for the plurality of highly absorbent layers is felt to be critical. Particularly suitable and preferred fabric for the manufacture of the highly absorbent center layers is a spunlaced water-absorbent fabric comprising a mixture acrylic and cellulosic fibers consisting essentially of about 25 to less than 50 percent, by weight, of crimped antimicrobial acrylic fibers having a dpf of about 0.75 to about 3.0 and a length from about 0.75 to about 3.0 inches and about 75 to greater than 50 percent of crimped hydrophilic cellulosic fibers having a dpf of about 0.75 to about 3.0 and a length from about 0.75 to about 3.0 inches as generally disclosed in U.S. Pat. No. 5,350,625 and marketed by E.I. Du Pont de Nemours & Company under the name "COMFORSORB".

EXAMPLE

To further illustrate and evaluate the improved adult incontinent absorbent undergarment according to the present invention, a garment as shown in the drawing was assembled using the respective layers of fabric as listed in the following Table. The dimensions of the hour-glass shaped insert were approximately 60 cm along the middle stitching of the four layers of "COMFORSORB" XM and open knit layer and approximately 27 cm wide at the front and rear of the panty with the free-floating crotch being 13 cm in length for both the 8 cm of pad and 10 cm of gathered non-woven urethane coated outer layer at the crotch.

TABLE

| Layer(s) | Fabric Employed |
| --- | --- |
| Outer Panty | A "COMFORSPAN" incontinence panty fabric made from a "XYMID" style 4078 comfomable fabric characterized as having a nominal finished weight per unit area of 4.5 oz/yd$^2$ (ASTM D3776) and elongation of 65 @ 200 g; 85 @ 500 g; & 100 @ 1000 g (ASTM D3107) constructed of a spunlaced "TENCEL" rayon fabric stitchbonded with 70/34 (denier/filament) textured nylon surface yarn and 140/40 (denier/denier) "LYCRA"/nylon stitching yarn. |
| Inner most layer of hour-glass shaped Insert | "COOLMAX" open knit polyester fabric manufactured from four channel fiber to enhance wicking of moisture |
| center four layers of hour-glass shaped Insert | "COMFORSORB" XM a 4 oz/yd$^2$ spunlaced water-absorbent fabric comprising a mixture 35% by weight antimicrobial acrylic fibers and 65% solvent spun unmodified cellulosic fibers "TENCEL" rayon fibers) manufactured according to U.S. Pat. No. 5,350,625 |
| outer most layer of hour-glass shaped Insert | A "COMFORSPAN" incontinence gusset fabric made from a "XYMID" style 4076 comfortable fabric characterized as having a nominal finished weight per unit area of 2.0 oz/yd$^2$ with a water impermeable layer of polyurethane on the outside surface. |

Comparative testing of the above described adult incontinent absorbent undergarment according to the present invention and selected AI undergarments commercially available in the market place indicated significant propensity with all competitive products to leak relative to the garment of the instant invention.

The advantages and benefits associated with the adult incontinent absorbent tradergarment according to the instant invention are felt to be numerous and significant. For example, the overall construction of the undergarment is amenable to conventional manufacturing techniques. The construction also affords the opportunity to readily vary the number of layers of highly absorbent fabric thus allowing for the manufacture of a series of undergarments that differ in level of absorbency; i.e., heavy, medium and light duty. Also, the independent construction of the absorbent pad affords the opportunity to incorporate antimicrobial fibers into the insert. The choice of fabric materials leads to rapid delivery of body fluids and simultaneous absorption as well as wicking through the pad and confinement of the liquid within the garment during absorption. The garment is reusable, conforms well to the body during use and exhibits an improved propensity not to leak.

Having thus described and exemplified the invention with a certain degree of particularity, it should be appreciated that the following claims are not to be so limited but are to be afforded a scope commensurate with the wording of each element of the claim and equivalents thereof.

I claim:

1. An adult incontinent undergarment comprising:
   (a) an outer panty having elastic top around the waist and elastic edging around the leg holes wherein said outer panty fabric consists of a conformable, stretchable fabric that is absorbent and adapted to wick moisture; and
   (b) an inner hour-glass shaped insert operatively attached to the inside surface of said panty at the perimeter of the large ends of said hour-glass shaped insert to the back and front area of said panty, respectively, and not operatively attached to the inside surface of said outer panty at the narrow portion of the hour-glass shaped insert to the crotch of said panty wherein said hour-glass shaped insert comprises:
      (i) an inner most wicking layer of open knit fabric for making contact to the skin;
      (ii) a plurality of center layers of spunlaced fabric comprising a blend of antimicrobial acrylic fibers and hydrophilic cellulosic fibers, wherein the edges of said plurality of layers and said open knit layer are stitched together in the region of the crotch forming a separate free-floating absorbent fabric pad at the crotch; and
      (iii) a outer most layer of non-woven, conformable fabric, wherein the outer surface of said non-woven fabric is laminated with a moisture impermeable coating of urethane and the edges of said non-woven fabric are stitched around individual elastic bands in the region of the crotch that tend to gather the urethane coated non-woven, conformable fabric forming a separate free-floating waterproof barrier between the panty and said absorbent fabric pad at the crotch, wherein said inner hour-glass shaped insert further comprises two to six center layers of a spunlaced water-absorbent fabric comprising a mixture acrylic and cellulosic fibers consisting essentially of from about 25 to less than 50 percent, by weight, of crimped antimicrobial acrylic fibers having a dpf of from about 0.75 to about 3.0 and a length from about 0.75 to about 3.0 inches and from about 75 to greater than 50 percent of crimped hydrophilic cellulosic fibers having a dpf of about from 0.75 to about 3.0 and a length from about 0.75 to about 3.0 inches.

2. An adult incontinent undergarment according to claim 1 wherein the inner hour-glass shaped insert is operatively attached to the inside surface of said outer panty by stitching the perimeter of the large ends of said hour-glass shaped insert to the back and to the front area of said outer panty.

3. An adult incontinent undergarment according to claim 1 wherein the inner hour-glass shaped insert is operatively attached to the inside surface of said outer panty by the use of fasteners located at the perimeter of the large ends of said hour-glass shaped insert and at the back and the front area of said outer panty.

4. An adult incontinent undergarment according to claim 1 wherein said inner most wicking layer of open knit fabric for making contact to the skin is polyester fabric made of four-channel fiber.

* * * * *